(12) United States Patent
Yazawa et al.

(10) Patent No.: US 7,968,116 B2
(45) Date of Patent: Jun. 28, 2011

(54) ANTITUMOR AGENT

(75) Inventors: Shin Yazawa, Tokushima (JP); Touyou Nishimura, Tokushima (JP); Takashi Nakagawa, Chiyoda-ku (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 653 days.

(21) Appl. No.: 11/997,579

(22) PCT Filed: Sep. 1, 2006

(86) PCT No.: PCT/JP2006/317316
§ 371 (c)(1),
(2), (4) Date: Feb. 1, 2008

(87) PCT Pub. No.: WO2007/026869
PCT Pub. Date: Mar. 8, 2007

(65) Prior Publication Data
US 2010/0292176 A1 Nov. 18, 2010

(30) Foreign Application Priority Data
Sep. 2, 2005 (JP) ................. 2005-255517

(51) Int. Cl.
*A61K 9/127* (2006.01)
*A61K 31/704* (2006.01)
*A61K 31/724* (2006.01)
(52) U.S. Cl. ............................ 424/450; 514/26; 514/58
(58) Field of Classification Search .................. None
See application file for complete search history.

(56) References Cited

U.S. PATENT DOCUMENTS
2006/0193903 A1  8/2006  Yazawa et al.

FOREIGN PATENT DOCUMENTS
| JP | 57 2300 | 1/1982 |
| JP | 11 60592 | 3/1999 |
| JP | 2000 191685 | 7/2000 |
| WO | WO 2005/007172 | 1/2005 |

OTHER PUBLICATIONS

Pitha, J. et al "Amorphous water-soluble derivatives of cyclodextrins . . . " J. Pharm. Sci. (1985) vol. 74, No. 9, pp. 987-990.*
STN abstract of Dong et al, CN 1393484 (2003).*
Junichi Goto, et al., "Synthesis of Conjugated Cholesterol and Cholestanols", Chem. Pharm. Bull., vol. 27, No. 8, pp. 1926-1931, 1979.
U.S. Appl. No. 12/553,355, filed Sep. 3, 2009, Yazawa, et al.

* cited by examiner

*Primary Examiner* — Leigh C Maier
(74) *Attorney, Agent, or Firm* — Oblon, Spivak, McClelland, Maier & Neustadt, L.L.P.

(57) ABSTRACT

A sugar-cholestanol compound which can be readily synthesized and which exhibits a satisfactory antitumor activity. An anticancer agent containing, as an active ingredient, a cholestanol compound represented by the following formula (1):

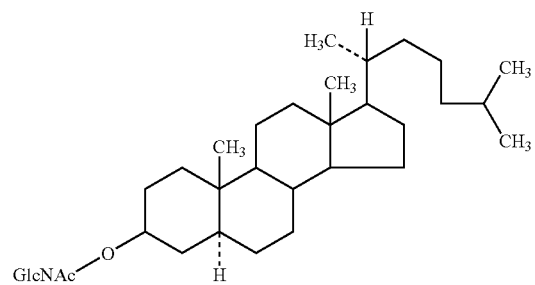

or a cyclodextrin inclusion complexation containing the compound. A method for treating cancer using this compound.

10 Claims, No Drawings

ANTITUMOR AGENT

TECHNICAL FIELD

The present invention relates to a drug containing a sugar-cholestanol compound as an active ingredient.

BACKGROUND ART

A sugar-cholestanol compound, in which GlcNAc-Gal-, GlcNAc-Gal-Glc-, Fuc-Gal-, Gal-Glc-, or Gal- is binding to cholestanol having a saturated carbon-carbon double bond in the B ring of cholesterol, exhibits an excellent antitumor activity (see Patent Documents 1, 2, and 3).

Most of such sugar-cholestanol compounds consisting of at least two sugar-chain moieties exhibit antitumor activities. However, these compounds require a complicated process for synthesis and a higher production cost as the number of sugar-chain moieties increases. Meanwhile, a sugar-cholestanol compound having galactose as a single sugar moiety has been reported so far, but its activity has still been unsatisfactory. Furthermore, those sugar-cholestanol compounds share the same problem in that they are generally water-insoluble.

Thus there has been a growing demand for a new sugar-cholestanol compound which has a small number of short sugar chain moieties, exhibits enough anticancer activity, and is excellent in solubility.

A cholestanol compound having N-acetyl-D-glucosamine (GlcNAc) as a sugar-chain moiety is a known compound (see Non-Patent Document 1), but no report has yet been made to its bioactivity.

[Patent Document 1] JP-A-11-60592

[Patent Document 2] JP-A-2000-191685

[Patent Document 3] WO 2005/007172 pamphlet

[Non-Patent Document 1] Studies on steroids. Part CXXXXV. Synthesis of conjugated cholesterol and cholestanols. (1979), 27 (8), 1926-31.

DISCLOSURE OF THE INVENTION

Problems to be Solved by the Invention

An object of the present invention is to provide a sugar-cholestanol compound which can be readily synthesized, and which exhibits satisfactory antitumor activity.

Means for Solving the Problems

In a sugar-cholestanol, no antitumor activity is recognized about either its sugar-chain moiety or cholestanol moiety at all, so the entire structure of sugar-cholestanol is essential for expression of antitumor activity. But it has been extremely difficult to deduce the number or type of sugar-chain moieties from the correlated structure. Under such a circumstance, the present inventors have found that a cholestanol compound represented by the below-described formula (1), which has GlcNAc as a single sugar moiety, exhibits a strong inhibitory activity against cancer cell growth. The present inventors have also found that the cholestanol compound, when in a form of a cyclodextrin inclusion complexation or a liposomal preparation, can overcome the drawback attributable to insolubility, and that this compound is much more effective in respect of the aforementioned activity.

Accordingly, the present invention provides the following.

1) An anticancer agent containing, as an active ingredient, a cholestanol compound represented by the following formula (1):

[F1]

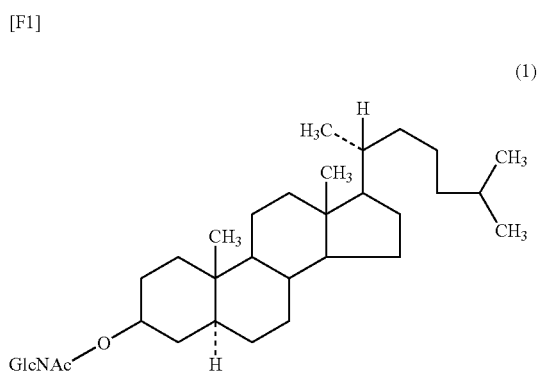

or a cyclodextrin inclusion complexation containing the compound.

2) A liposomal formulation containing the cholestanol compound.

3) A cyclodextrin inclusion complexation containing the cholestanol compound.

4) Use of the cholestanol compound or a cyclodextrin inclusion complexation containing the compound for producing an anticancer agent.

5) A method for preventing or treating cancer, characterized by comprising administration of the cholestanol compound or a cyclodextrin inclusion complexation containing the compound.

Effects of the Invention

The cholestanol compound of the present invention exhibits excellent antitumor effects, and can be readily synthesized as compared with the case of a conventional sugar-cholestanol compound. Therefore, the cholestanol compound of the present invention is useful as a drug for preventing or treating cancer. A cyclodextrin inclusion complexation or liposomal formulation containing the cholestanol compound exhibits excellent solubility, and is remarkably effective in that the compound exhibits anticancer activity.

BEST MODE FOR CARRYING OUT THE INVENTION

The cholestanol compound of the present invention, which is a known compound (see Non-Patent Document 1), can be produced by, for example, the following method.

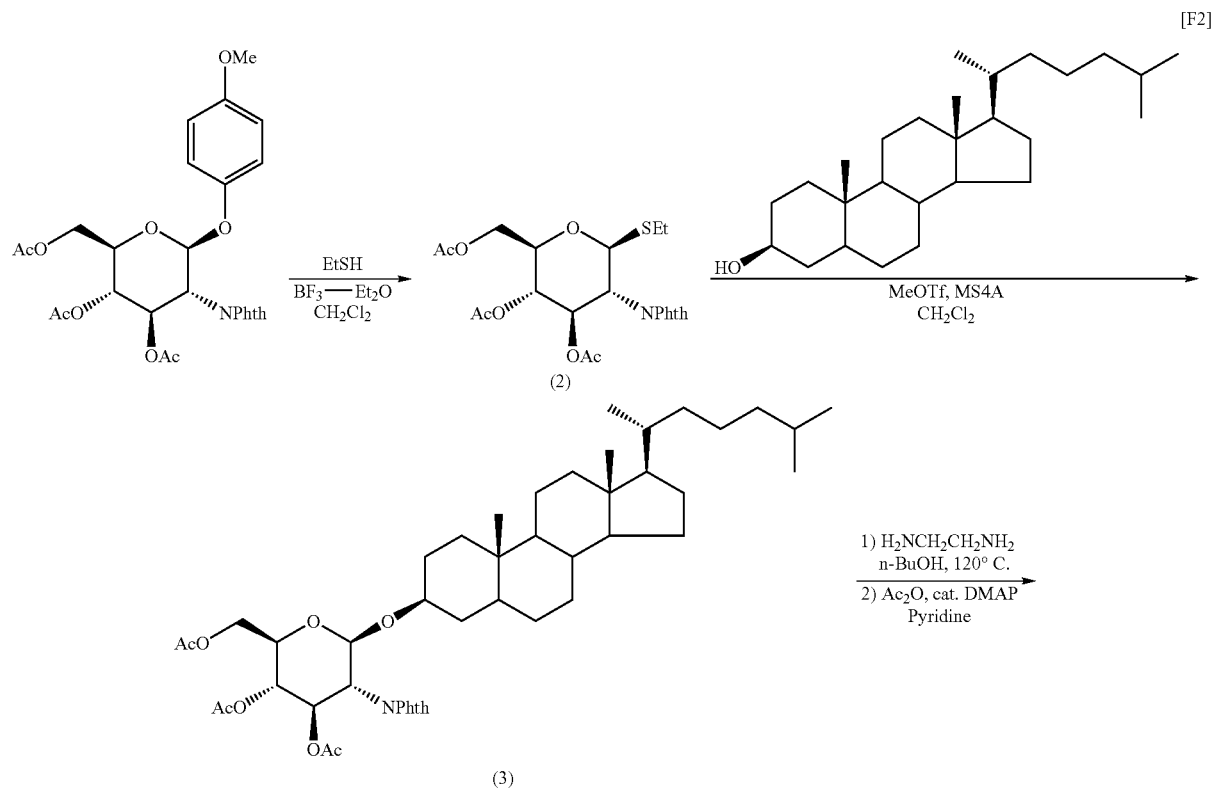
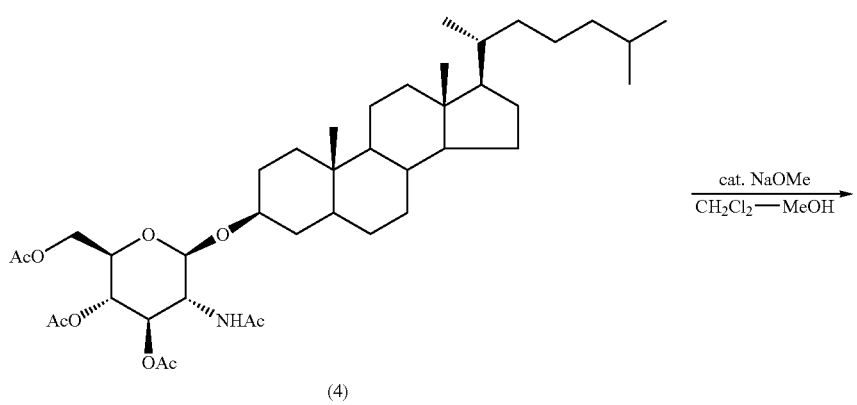
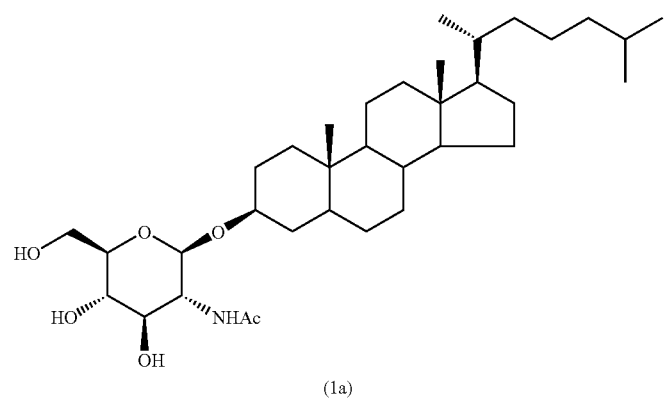

Specifically, the cholestanol compound of the present invention can be produced from 4-methoxyphenyl-3,4,6-tri-O-acetyl-2-deoxy-2-phthalimido-β-D-glucopyranoside through four steps (see the below-described Production Example).

The sugar-chain moiety of the cholestanol compound of the present invention is preferably GlcNAcβ-. Therefore, the cholestanol compound of the present invention is preferably 5-α-cholestan-3β-yl-2-acetamido-2-deoxy-β-D-glucopyranoside (1a).

The cholestanol compound of the present invention can be readily included in a cyclodextrin compound or a derivative thereof to form a complex. Cyclodextrin is not necessarily adapted to all insoluble compounds, since, conceivably, formation of a cyclodextrin inclusion complexation is affected by the size of a guest molecule to be included, the van der Waals interaction between the guest molecule and cyclodextrin, or the hydrogen bonding between the guest molecule and hydroxyl groups of cyclodextrin. However, cyclodextrin can form a good inclusion complex with the cholestanol compound of the present invention.

Examples of the cyclodextrin employed for forming the cyclodextrin inclusion complexation of the present invention include cyclodextrin compounds such as α-cyclodextrin, β-cyclodextrin, and γ-cyclodextrin; and cyclodextrin derivatives such as methyl-β-cyclodextrin, 2-hydroxypropyl-β-cyclodextrin, monoacetyl-β-cyclodextrin, and 2-hydroxypropyl-γ-cyclodextrin. Of these, 2-hydroxypropyl-β-cyclodextrin is preferred for obtaining improved solubility.

The cyclodextrin inclusion complexation can be prepared through, for example, the following procedure: an appropriate aqueous solution (e.g., 20 to 40%) of a cyclodextrin compound or a derivative thereof is prepared, and the cholestanol compound of the present invention is added to the aqueous solution, followed by stirring of the resultant mixture.

No particular limitation is imposed on the amount of the cholestanol compound to be added, so long as the cholestanol compound can form an inclusion complex with cyclodextrin. The amount is generally 1 to 50 mass %, preferably about 10 to about 30 mass %.

The thus-formed cyclodextrin inclusion complexation is readily soluble in water, and therefore exhibits its effects efficiently in vivo. The cyclodextrin inclusion complexation is also advantageous in that it can be reliably evaluated in an in vitro test system.

A liposomal formulation prepared from the cholestanol compound of the present invention can be efficiently delivered to a site where the effects of the compound are to be exhibited. The liposomal formulation can also be reliably evaluated in an in vitro test system.

The liposomal formulation preferably contains the cholestanol compound of the present invention, a membrane component, and an aliphatic or aromatic amine.

The amount of the cholestanol compound contained in the liposomal formulation is 0.3 to 2.0 mol, preferably 0.8 to 1.5 mol, on the basis of 1 mol of the membrane component.

Examples of the membrane component include phospholipids. Phospholipids which are preferably employed include naturally occurring and synthesized phospholipids such as phosphatidylcholine, phosphatidylethanolamine, phosphatidylserine, phosphatidylinositol, and phosphatidic acid; mixtures of these phospholipids; and processed naturally occurring phospholipids such as aqueous lecithin. More preferably, 1α-dipalmitoylphosphatidylcholine (DPPC), which is a phosphatidylcholine compound, is employed.

The aliphatic or aromatic amine is generally added for positively charging the surface of a lipid membrane. Examples of the amine to be added include aliphatic amines such as stearylamine and oleylamine; and aromatic amines such as fluoreneethylamine. Particularly, stearylamine is preferably employed.

The amount of the amine contained in the liposomal formulation is 0.04 to 0.15 mol, preferably 0.1 to 0.15 mol, on the basis of 1 mol of the membrane component (phospholipid).

If necessary, the liposomal formulation may contain, in addition to the aforementioned components, a membrane structure stabilizer such as cholesterol, a fatty acid, or diacetyl phosphate.

The aqueous solution employed for dispersing the membrane component is preferably water, saline, a buffer, an aqueous solution of a sugar, or a mixture thereof. The buffer to be employed is preferably an organic or inorganic buffer which has buffering action in the vicinity of the hydrogen ion concentration of body fluids. For example, a phosphate buffer can be employed.

No particular limitation is imposed on the method for preparing the liposomal formulation, and the formulation can be prepared through a generally employed method. For example, the liposomal formulation can be prepared through the method described in JP-A-57-82310, JP-A-60-12127, JP-A-60-58915, JP-A-1-117824, JP-A-1-167218, JP-A-4-29925, or JP-A-9-87168, the method described in Methods of Biochemical Analysis (1988) 33, p 337, or the method described in "Liposome" (Nankodo).

Next will be described a procedure for preparing a liposomal formulation from the cholestanol compound of the present invention.

Firstly, an organic solvent and water are added to and mixed with the cholestanol compound of the present invention, any of the aforementioned membrane components, and an aliphatic or aromatic amine, and subsequently the organic solvent is completely removed by means of a rotary evaporator or a similar apparatus, followed by removal of water.

The mixing proportions of the membrane component, the alkylamine, and the cholestanol compound may be, for example, 52:8:20 (by mole). However, so long as the mixing proportions do not deviate significantly therefrom, no particular problems would arise. When the mixing proportion of the cholestanol compound is low, if necessary, a membrane structure stabilizer such as cholesterol may be added. However, when the mixing proportion of the cholestanol compound is high, addition of such a membrane structure stabilizer is not necessarily required.

No particular limitation is imposed on the organic solvent to be employed, so long as it is a volatile organic solvent which is insoluble in water. Examples of the organic solvent which may be employed include chloroform, chloromethane, benzene, and hexane. In consideration of solubility, an organic solvent having relatively high polarity (e.g., ethanol or methanol) may be appropriately added to such a water-insoluble solvent, and the thus-prepared organic solvent mixture may be employed. No particular limitation is imposed on the mixing proportions of the organic solvent mixture and water, so long as a uniform solvent mixture is obtained.

In the case where water is added for preparation of the liposomal formulation, removal of water is generally carried out through freeze-drying. However, removal of water is not necessarily performed through freeze-drying, and may be performed through drying in a reduced-pressure desiccator. After removal of water, the aforementioned aqueous solution for dispersion is added, followed by shaking by means of, for example, a Vortex mixer, to thereby form the liposomal formulation.

Liposomes having a uniform particle size can be prepared through, for example, ultrasonic treatment, extrusion treatment by means of a porous membrane filter, treatment by means of a high-pressure injection emulsifier, or combination of such treatments. Smaller liposome particles can be prepared by, for example, performing ultrasonic treatment for a long period of time. The particle size of liposomes is preferably 40 nm to 300 nm.

The cholestanol compound of the present invention can be employed in the form, in addition to the aforementioned liposomal formulation, of a variety of stabilizers, and the stabilizer form varies in response to a dosage form to be employed.

As described below in Examples, the cholestanol compound of the present invention, a cyclodextrin inclusion complexation containing the cholestanol compound, and a liposomal formulation containing the cholestanol compound (hereinafter these may be collectively referred to as "the cholestanol compound, etc.") exhibit much stronger cell proliferation inhibitory effect, as compared with the case of a cholestanol compound having a sugar-chain moiety formed of GlcNAc-Gal- or Gal-. Therefore, a formulation containing, as an active ingredient, the cholestanol compound of the present invention is useful as a drug for preventing or treating cancer.

The dosage form of the anticancer agent of the present invention can be appropriately determined in consideration of the treatment site or the therapeutic purpose. So long as an additive which impedes the stability of the form of the liposomal formulation is not employed, the anticancer agent may be in any dosage form of, for example, a peroral product, an injection, a suppository, an ointment, and a patch, each of which can be produced through a conventional formulation method known to those skilled in the art.

A peroral solid product (e.g., a tablet, a coated tablet, a granule, a powder, or a capsule) can be prepared by adding, to the cholestanol compound, etc. of the present invention, an excipient and, if necessary, an additive such as a binder, a disintegrating agent, a lubricant, a coloring agent, a flavoring agent, or a deodorant, followed by customary processing. The additive to be employed may be an additive which is generally used in the art. Examples of the excipient include lactose, sucrose, sodium chloride, glucose, starch, calcium carbonate, kaolin, microcrystalline cellulose, and silicic acid. Examples of the binder include water, ethanol, propanol, simple syrup, liquid glucose, liquid starch, liquid gelatin, carboxymethyl cellulose, hydroxypropyl cellulose, hydroxypropyl starch, methyl cellulose, ethyl cellulose, shellac, calcium phosphate, and polyvinyl pyrrolidone. Examples of the disintegrating agent include dry starch, sodium alginate, agar powder, sodium hydrogencarbonate, calcium carbonate, sodium lauryl sulfate, monoglyceride stearate, and lactose. Examples of the lubricant include purified talc, stearic acid salts, borax, and polyethylene glycol. Examples of the flavoring agent include sucrose, orange peel, citric acid, and tartaric acid.

A peroral liquid product (e.g., a peroral solution, a syrup, or an elixir) can be prepared by adding, to the cholestanol compound, etc. of the present invention, a flavoring agent, a buffer, a stabilizer, a deodorant, or the like, followed by customary processing. The flavoring agent to be employed for this preparation may be any of the aforementioned ones. Examples of the buffer include sodium citrate. Examples of the stabilizer include tragacanth, gum arabi, and gelatin.

An injection (e.g., a subcutaneous injection, an intramuscular injection, or an intravenous injection) can be prepared by adding, to the cholestanol compound, etc. of the present invention, a pH-adjusting agent, a buffer, a stabilizer, an isotonizing agent, a local anesthetic agent, or the like, followed by customary processing. Examples of the pH-adjusting agent and the buffer employed for this preparation include sodium citrate, sodium acetate, and sodium phosphate. Examples of the stabilizer include sodium pyrosulfite, EDTA, thioglycolic acid, and thiolactic acid. Examples of the local anesthetic agent include procaine hydrochloride and lidocaine hydrochloride. Examples of the isotonizing agent include sodium chloride and glucose.

A suppository can be prepared by adding, to the cholestanol compound, etc. of the present invention, a carrier for drug preparation known in the art, such as polyethylene glycol, lanolin, cocoa butter, or fatty acid triglyceride, and, if necessary, a surfactant such as Tween (registered trademark), followed by customary processing.

An ointment is prepared by mixing, through a customary technique, the cholestanol compound, etc. of the present invention with, if necessary, a generally employed additive such as a base, a stabilizer, a humectant, or a preservative. Examples of the base include liquid paraffin, white petrolatum, white beeswax, octyldodecyl alcohol, and paraffin. Examples of the preservative include methyl p-hydroxybenzoate, ethyl p-hydroxybenzoate, and propyl p-hydroxybenzoate.

A patch can be prepared by applying, to a generally employed support, the aforementioned ointment and a cream, a gel, a paste, or the like. Examples of appropriate supports include woven fabrics and non-woven fabrics formed of cotton, staple fiber, and chemical fiber; and films and foam sheets formed of soft vinyl chloride, polyethylene, and polyurethane.

The dose of the cholestanol compound, etc. of the present invention varies depending on the symptom, body weight, age, sex, etc. of a patient in need thereof. The daily dose of the cholestanol compound, etc. for an adult is typically about 0.01 to about 200 mg/kg, preferably 0.1 to 50 mg/kg, as reduced to the cholestanol compound (1). Preferably, the daily dose is administered once a day, or in a divided manner (2 to 4 times a day).

The present invention will next be described in more detail by way of Examples.

EXAMPLES

Production Example 1

Production of GlcNAc-cholestanol (1) Production of ethyl-3,4,6-tri-O-acetyl-2-deoxy-2-phthalimido-1-thio-β-D-glucopyranoside (compound (2))

In an argon atmosphere, a solution of 4-methoxyphenyl-3,4,6-tri-O-acetyl-2-deoxy-2-phthalimido-β-D-glucopyranoside (2 g, 4.19 mmol) and ethanethiol (0.40 mL, 5.45 mmol) in dry methylene chloride (30 mL) was ice-cooled, and boron trifluoride-diethyl ether complex (3.19 mL, 25.14 mmol) was added dropwise to the solution, followed by stirring at room temperature overnight. A saturated aqueous sodium hydrogencarbonate solution was added to the resultant reaction mixture under ice cooling, and the resultant organic layer was dried over sodium sulfate. The solvent was removed through evaporation under reduced pressure, and the residue was recrystallized from ethyl acetate-hexane, to thereby yield 1.62 g of the title compound.

Form: white powder;
$^1$H-NMR (CDCl$_3$) δ: 1.22 (3H, t, J=7.3 Hz), 1.86 (3H, s), 2.04 (3H, s), 2.11 (3H, s), 2.61-2.76 (2H, m), 3.90 (1H, ddd, J=2.4 Hz, 4.9 Hz, 10.3 Hz), 4.18 (1H, dd, J=2.2 Hz, 12.4 Hz), 4.31 (1H, dd, J=2.2 Hz, 12.4 Hz), 4.39 (1H, dd, J=10.3 Hz, 10.3 Hz), 5.18 (1H, dd, J=9.2 Hz, 10.3 Hz), 5.49 (1H, d, J=10.3 Hz), 5.83 (1H, dd, J=9.2 Hz, 10.3 Hz), 7.74 (2H, dd, J=2.4 Hz, 5.4 Hz), 7.86 (2H, dd, J=2.4 Hz, 5.4 Hz).

(2) Production of 5-α-cholestan-3β-yl-2-deoxy-2-phthalimido-3,4,6-tri-O-acetyl-β-D-glucopyranoside (compound (3))

In an argon atmosphere, dried ethylene chloride (4.6 mL) was added to a mixture of the compound (2) obtained in (1) above (400 mg, 0.834 mmol), 5-α-cholestan-3β-ol (389 mg, 1.0 mmol), and activated molecular sieves 4A (1.88 g), followed by stirring at room temperature for one hour. Subsequently, methyl trifluoromethanesulfonate (0.28 mL, 2.48 mmol) was added to the resultant mixture, followed by stirring overnight. Triethylamine (1 mL) was added to the resultant reaction mixture, followed by stirring for 30 minutes. Thereafter, the resultant mixture was subjected to celite filtration, and the filtrate was washed with methylene chloride. The solvent was removed through evaporation from a mixture of the filtrate and the washing liquid, and the residue was purified by means of silica gel column chromatography (hexane:ethyl acetate=3:1 (by volume), the same shall apply hereinafter), to thereby yield 510 mg of the title compound.

Form: white powder;
$^1$H-NMR (CDCl$_3$) δ: 0.51-2.10 (55H, m), 3.48-3.56 (1H, m), 3.85 (1H, ddd, J=2.4 Hz, 4.9 Hz, 10.3 Hz), 4.15 (1H, dd, J=2.2 Hz, 12.2 Hz), 4.26-4.34 (3H, m), 5.15 (1H, dd, J=8.9 Hz, 10.0 Hz), 5.46 (1H, d, J=8.4 Hz), 5.77 (1H, dd, J=8.9 Hz, 10.8 Hz), 7.74 (2H, dd, J=2.4 Hz, 5.4 Hz), 7.86 (2H, dd, J=2.4 Hz, 5.4 Hz).

(3) Production of 5-α-cholestan-3β-yl-2-acetamido-2-deoxy-3,4,6-tri-O-acetyl-β-D-glucopyranoside (compound (4))

Ethylenediamine (5.0 mL) was added to a suspension of the compound (3) obtained in (2) above (510 mg, 0.633 mmol) in 1-butanol (5.0 mL), and the resultant mixture was stirred at 120° C. overnight. The solvent was removed from the reaction mixture through evaporation under reduced pressure, and the residue was mixed with pyridine (5 mL), acetic anhydride (5 mL), and 4-dimethylaminopyridine (catalytic amount), followed by stirring overnight. The solvent was removed from the reaction mixture through evaporation under reduced pressure, and the residue was dissolved in ethyl acetate. The resultant solution was washed with 1 M aqueous hydrochloric acid solution, a saturated aqueous sodium hydrogencarbonate solution, and a saturated aqueous saline, and then the resultant organic layer was dried over sodium sulfate. The solvent was removed through evaporation under reduced pressure, and the residue was purified by means of silica gel column chromatography (hexane:ethyl acetate=1:4), to thereby yield 250 mg of the title compound.

Form: white powder;
$^1$H-NMR (CDCl$_3$) δ: 0.55-2.07 (58H, m), 3.52-3.72 (3H, m), 4.10 (1H, dd, J=2.2 Hz, 11.3 Hz), 4.26 (1H, dd, J=2.2 Hz, 12.2 Hz), 4.86 (1H, d, J=8.4 Hz), 5.03 (1H, dd, J=9.7 Hz, 9.7 Hz), 5.35-5.43 (2H, m).

(4) Production of 5-α-cholestan-3β-yl-2-acetamido-2-deoxy-β-D-glucopyranoside (compound (1a))

28% Sodium methoxide methanol solution (0.07 mL, 0.363 mmol) was added to a solution of the compound (4) obtained in (3) above (250 mg, 0.348 mmol) in a mixture of methanol (5.0 mL) and methylene chloride (5.0 mL), followed by stirring at room temperature overnight. The resultant reaction mixture was neutralized with Amberlyst 15, and then the reaction mixture was subjected to filtration. The solvent was removed from the filtrate through evaporation under reduced pressure, and the residue was suspended in methanol. Insoluble matters obtained through filtration was washed with methanol, and then dried, to thereby yield 159 mg of the title compound.

Form: white powder;
$^1$H-NMR (DMSO-d$_6$+D$_{20}$) δ: 0.62-1.94 (49H, m), 2.99-3.05 (2H, m), 3.22-3.50 (4H, m), 3.66 (1H, d, J=11.6 Hz), 4.40 (1H, d, J=7.6 Hz), 7.64 (1H, d, J=8.4 Hz).

Example 1

Production of Liposomal Formulation and Cyclodextrin Inclusion Complexation

A 20 µmol/mL solution of each of GlcNAc-cholestanol (compound (1a)) and cholestanol (dissolved in chloroform/methanol=5/1 (v/v)) was employed as a starting material.

(1) Preparation of Liposomal Formulation

1α-Dipalmitoylphosphatidylcholine, stearylamine, and sugar-cholestanol were mixed in proportions of 52/8/20 (by mole) so as to attain a total amount of 700 µL, and subsequently an organic solvent (chloroform/methanol=2/1 (V/V)) (300 µL) and distilled water (1 mL) were added to and mixed with the resultant mixture. Thereafter, the oryganic solvent was completely removed by means of a rotary evaporator, and the resultant product was subjected to freeze-drying, to thereby completely remove water. The freeze-dried product was dissolved in PBS (1 mL), followed by ultrasonic treatment (15 W, 15 minutes), to thereby form liposomes having a uniform particle size of about 40 to about 300 nm. The thus-formed liposomes were employed in Example 2.

(2) Preparation of Cyclodextrin Inclusion Complexation

20% Aqueous hydroxypropyl-β-cyclodextrin solution was prepared, and GlcNAc-cholestanol was added to the solution, followed by stirring/mixing, to thereby form an inclusion complex of cyclodextrin with GlcNAc-cholestanol. Formation of a good inclusion complex is confirmed by observing that GlcNAc-cholestanol (i.e., an insoluble compound) is solubilized through stirring.

Example 2

Cell Proliferation Inhibitory Effect of GlcNAc-Cholestanol

A cultured cancer cell line (HT-29 (human)) was inoculated into a 96-well plate (1×10$^4$ cells/100 µL/well), and subsequently the GlcNAc-cholestanol-compound-containing liposomal formulation or cyclodextrin inclusion complexation prepared in Example 1 was added to the 96-well plate, followed by incubation at 37° C. for three days. Thereafter, the MTT assay was performed, and the number of cells was determined. Percent cell proliferation inhibition was obtained by use of the below-described formula. The results are shown in Table 1.

As a result, the GlcNAc-cholestanol exhibited strong cell proliferation inhibitory effect.

Percent cell proliferation inhibition (percent *CPI*)
(%)=(1−*OD* of treated cells/*OD* of non-treated cells)×100    [E1]

OD of treated cells and OD of non-treated cells were measured at 450 nm and 650 nm, respectively (according to the MTT assay).

TABLE 1

Cell proliferation inhibitory effect of sugar-cholestanol

| Sugar-cholestanol[1] | Form | CPI50(µM)[2] |
|---|---|---|
| GlcNAcGalChol | Liposomal formulation | 10.2 |
| GlcNacChol | Liposomal formulation | 10.4 |
| GalChol | Liposomal formulation | 12.7 |
| Chol | Liposomal formulation | 354.3 |
| GlcNAcGalChol | Cyclodextrin inclusion complexation | 15.9 |
| GlcNacChol | Cyclodextrin inclusion complexation | 8.8 |
| GalChol | Cyclodextrin inclusion complexation | 37.4 |
| Chol | Cyclodextrin inclusion complexation | >1000 |

[1]GlcNAcGalChol: GlcNAcβ1,3Galβ-cholestanol
GlcNacChol: GlcNAcβ-cholestanol
GalChol: Galp-cholestanol
Chol: cholestanol
[2]Concentration required for attaining 50% CPI

The invention claimed is:

1. A cyclodextrin inclusion complexation comprising a cholestanol compound represented by formula (1):

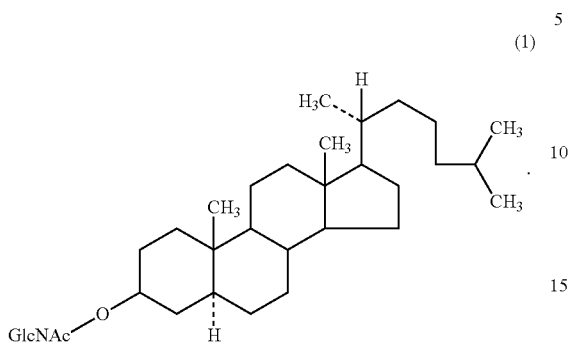

2. The cyclodextrin inclusion complexation according to claim 1 which contains 10% to 30% by mass of the cholestanol compound.

3. The cyclodextrin inclusion complexation of claim 2, wherein the cyclodextrin is 2-hydroxypropyl-β-cyclodextrin.

4. A method for making the cyclodextrin inclusion complexation of claim 1 comprising admixing cyclodextrin and a cholestanol compound represented by formula (1):

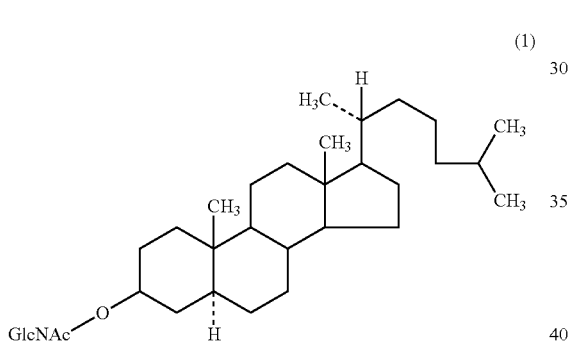

and recovering a cyclodextrin inclusion complexation.

5. A method for treating colon cancer sensitive to cholestanol comprising administering to a subject in need thereof the cyclodextrin inclusion complexation of claim 1.

6. A liposomal formulation comprising a cholestanol compound represented by formula (1):

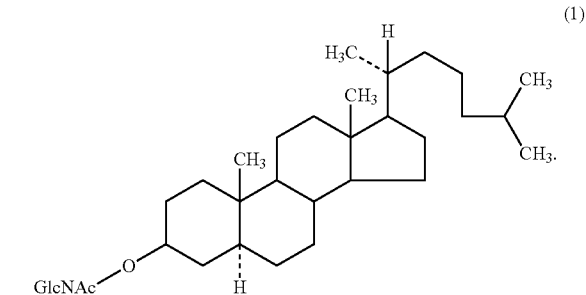

7. The liposomal formulation according to claim 6 which comprises the cholestanol compound, a membrane component, and an aliphatic or aromatic amine.

8. The liposomal formulation of claim 6, wherein the membrane component is a phospholipid.

9. A method for making the liposomal formulation of claim 6 comprising admixing a membrane component, an aliphatic or aromatic amine, and a cholestanol compound represented by formula (1):

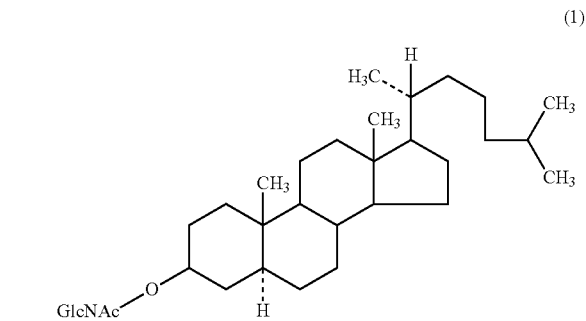

and recovering the liposomal formulation.

10. A method for treating colon cancer sensitive to cholestanol comprising administering to a subject in need thereof the liposomal formulation of claim 6.

* * * * *